United States Patent [19]

Lantzsch

[11] Patent Number: 5,352,794
[45] Date of Patent: Oct. 4, 1994

[54] PROCESS FOR THE PREPARATION OF N-(2-CHLORO-PYRIDIN-5-YL-METHYL)E-THYLENEDIAMINE

[75] Inventor: Reinhard Lantzsch, Wuppertal, Fed. Rep. of Germany

[73] Assignee: Bayer Aktiengesellschaft, Leverkusen, Fed. Rep. of Germany

[21] Appl. No.: 970,907

[22] Filed: Nov. 3, 1992

[30] Foreign Application Priority Data

Nov. 13, 1991 [DE] Fed. Rep. of Germany ....... 4137271

[51] Int. Cl.$^5$ ............................................ C07D 207/444
[52] U.S. Cl. .................................................... 546/329
[58] Field of Search ........................................ 546/329

[56] References Cited

U.S. PATENT DOCUMENTS 5,164,508  11/1992  Diehr ................................. 546/329

FOREIGN PATENT DOCUMENTS 0163855  4/1985  European Pat. Off. .
0192060  1/1986  European Pat. Off. .
0302389  7/1988  European Pat. Off. .
2232326  6/1974  France .

OTHER PUBLICATIONS

Jerzy Wolinski, Acta Polon. Pharm., 1980, pp. 501–505.
Milos Hudlicky, *Reductions in Organic Chemistry*, 1984, pp. 134–136.

*Primary Examiner*—C. Warren Ivy
*Assistant Examiner*—Raymond Covington
*Attorney, Agent, or Firm*—Sprung Horn Kramer & Woods

[57] ABSTRACT

The present invention relates to a new process for the preparation of N-(2-chloro-pyridin-5-yl-methyl)-ethylenediamine.

The process is characterised in that 6-chloronicotinaldehyde is reacted with 1,2-ethylenediamine and a reducing agent at temperatures between −30° C. and +50° C.

The reducing agents employed are preferably metal hydride complexes and, in particular, sodium borohydride.

N-(2-Chloro-pyridin-5-yl-methyl)-ethylenediamine, which is to be prepared by the process according to the invention, can be used as intermediate for the preparation of insecticides.

8 Claims, No Drawings

PROCESS FOR THE PREPARATION OF N-(2-CHLORO-PYRIDIN-5-YL-METHYL)ETHYLENEDIAMINE

The invention relates to a new process for the preparation of N-(2-chloro-pyridin-5-yl-methyl)-ethylenediamine.

It is known that N-(2-chloro-pyridin-5-yl-methyl)-ethylenediamine, an intermediate for insecticides, is obtained when 2-chloro-5-chloromethyl-pyridine is reacted with ethylenediamine in acetonitrile (compare EP-A 163,855, Example 1).

However, this reaction does not proceed with sufficient selectivity, resulting in a reduced yield of desired product.

There has now been found a process for the preparation of N-(2-chloro-pyridin-5-yl-methyl)-ethylenediamine, of the formula (I),

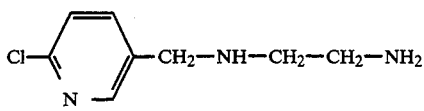

which is characterised in that 6-chloro-nicotinaldehyde, of the formula (II)

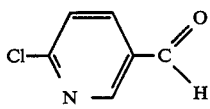

is reacted with 1,2-ethylenediamine, of the formula (III)

$$H_2N-CH_2-CH_2-NH_2 \qquad (III)$$

and a reducing agent in the presence of a diluent at temperatures between $-30°$ C. and $+50°$ C.

Surprisingly, N-(2-chloro-pyridin-5-yl-methyl)-ethylenediamine can be prepared by the process according to the invention in a technically simple manner in high yield and in good quality. This is because, as a comparison trial without the use of a reducing agent shows, a condensation reaction even on the second nitrogen atom of ethylenediamine must be expected, which, surprisingly, is avoided in the procedure according to the invention.

The course of the reaction in the process according to the invention can be outlined by the following equation:

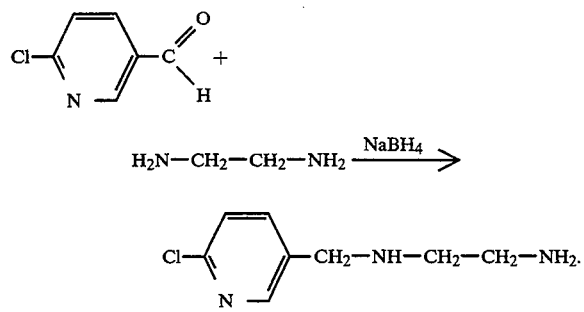

The 6-chloro-nicotinaldehyde, of the formula (II), which is to be used as starting material in the process according to the invention, has already been disclosed (compare, for example, EP-A 411,364).

Ethylenediamine, which is furthermore required as starting material, is a known chemical for synthesis.

The process according to the invention is carried out using a reducing agent. Reducing agents which are suitable in this context are, preferably, metal hydride complexes. Examples which may be mentioned are: lithium aluminium hydride (LiAlH$_4$), lithium borohydride (LiBH$_4$), sodium borohydride (NaBH$_4$) and potassium borohydride (KBH$_4$). The preferred reducing agent used in the process according to the invention is, in particular, sodium borohydride.

The process according to the invention is carried out using a diluent. Diluents which are preferably employed are polar solvents, in particular alcohols such as methanol, ethanol, propanol, isopropanol, butanol, isobutanol, sec-butanol and tert-butanol. A diluent which is very particularly preferred for the process according to the invention is methanol.

The reaction is carried out in the temperature range of from $-30°$ C. to $+50°$ C. It is preferably carried out at temperatures between $-10°$ C. and $+30°$ C.

The process according to the invention is generally carried out under atmospheric pressure. However, it is also possible to carry out the process under increased or reduced pressure - generally between 0.1 bar and 10 bar.

For carrying out the process according to the invention, between 1 and 5 moles, preferably between 2 and 4 moles, of ethylenediamine and between 0.5 and 3 moles, preferably between 1.0 and 1.5 moles, of reducing agent are generally employed per mole of 6-chloronicotinaldehyde of the formula (II).

In a preferred embodiment of the process according to the invention, the ethylenediamine is introduced into a diluent, and the solution of the 6-chloro-nicotinaldehyde is slowly added thereto. The mixture is briefly stirred, and the reducing agent is then slowly metered in, and the reaction mixture is stirred until the reaction is complete. Working-up can be carried out by customary methods (compare the Preparation Examples).

N-(2-Chloro-pyridin-5-yl-methyl)-ethylenediamine, which is to be prepared by the process according to the invention, can be used as intermediate for the preparation of insecticides (compare EP-A 163,855).

The following equation may be mentioned by way of example of the further reaction to obtain insecticidal active substances:

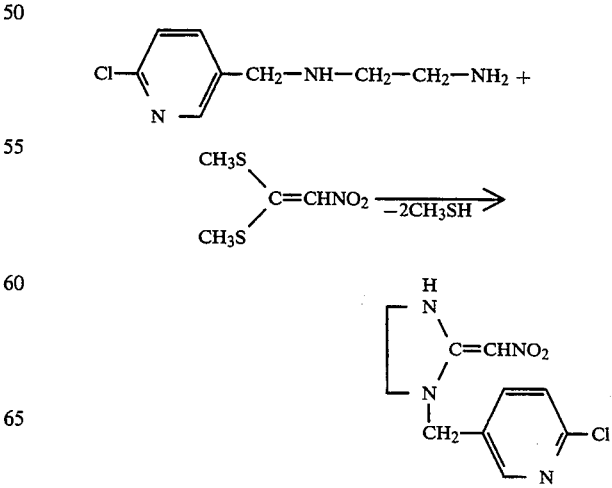

EXAMPLE 1

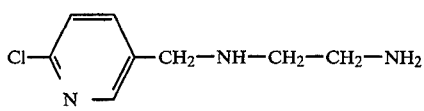

12 g (0.2 mol) of ethylenediamine in 70 ml of methanol are introduced into the reaction vessel. 7.1 g (0.05 mol) of 6-chloro-nicotinaldehyde, dissolved in 45 ml of methanol, is added dropwise at 0° C. Stirring is continued for 1 hour at 0° C., and 1.95 g (0.05 mol) of sodium borohydride are then added in portions, at 0° C. Stirring of the reaction mixture is continued for 12 hours without cooling, the reaction solution is filtered, and the filtrate is concentrated under a waterpump vacuum. The concentrated filtrate is treated with 50 ml of saturated sodium chloride solution and extracted four times using ethyl acetate. The combined extracts are dried with magnesium sulphate and concentrated in vacuo.

7.4 g of N-(2-chloro-pyridin-5-yl-methyl)-ethylenediamine of a purity of 94.2% (according to the gas chromatogram) are obtained. This corresponds to a yield of 75% of theory.

EXAMPLE 2

The reaction in Example 2 is carried out as described in Example 1. Working-up is carried out as follows: methanol and excess ethylenediamine are distilled off under a water pump vacuum, and the residue is taken up in water and filtered. According to HPLC analysis, this aqueous solutions contains 8.4 g (90.5% of theory) of N-(2-chloro-pyridin-5-yl-methyl)-ethylenediamine.

COMPARISON EXAMPLE

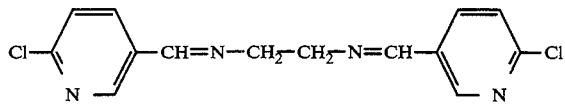

12 g (0.2 mol) of ethylenediamine in 70 ml of methanol are introduced into the reaction vessel. 7.1 g (0.05 mol) of 6-chloro-nicotinaldehyde, dissolved in 45 ml of methanol, are added dropwise at 0° C., and stirring is continued for 3 hours at 0° C. Methanol is distilled off in vacuo, the residue is taken up in approx. 100 ml of ethyl acetate, and the mixture is washed twice with sodium chloride solution. The organic phase is separated off, dried and concentrated.

5 g of N,N'-bis-(2-chloro-pyridin-5-yl-methylene)ethylenediamine of melting point 170° C. are obtained.

If the reaction time is shorter, the reaction mixture still contains unreacted starting material 6-chloronicotinaldehyde.

I claim:

1. Process for the preparation of N-(2-chloro-pyridin-5-yl-methyl)-ethylenediamine, of the formula (I),

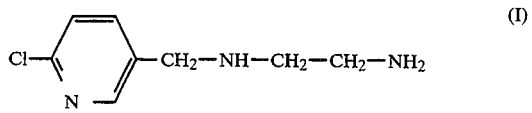

which comprises reacting 6-chloronicotinaldehyde, of the formula (II)

with about 1 to 5 times its molar amount of 1,2-ethylenediamine of the formula (III)

and about 0.5 to 3 times its molar amount of a reducing agent in the presence of an alcohol as diluent at a temperatures between −30° C. and +50° C.

2. Process according to claim 1, wherein a metal hydride complex compound is employed as the reducing agent.

3. Process according to claim 1, wherein a metal hydride complex compound from the series comprising lithium aluminium hydride, lithium borohydride, sodium borohydride and potassium borohydride is employed as the reducing agent.

4. Process according to claim 1, characterised in that sodium borohydride is employed as the reducing agent.

5. Process according to claim 1, wherein methanol is employed as the diluent.

6. Process according to claim 1, wherein the process is carried out at temperatures between −10° C. and +30° C.

7. Process according to claim 1, characterised in that 2 to 4 mols of 1,2-ethylenediamine and 1 to 1.5 mols of reducing agent are employed per mole of 6-chloronicotinaldehyde, of the formula (II).

8. Process according to claim 1, wherein the 1,2-ethylenediamine is introduced into a diluent, a solution of the 6-chloro-nicotinaldehyde is added slowly, the mixture is stirred briefly and the reducing agent is then slowly metered in, the reaction mixture is stirred until the reaction is complete, and the reaction product is worked up by customary methods.

* * * * *

UNITED STATES PATENT AND TRADEMARK OFFICE
CERTIFICATE OF CORRECTION

PATENT NO. : 5,352,794
DATED : October 4, 1994
INVENTOR(S) : Reinhard LANTZSCH

It is certified that error appears in the above-identified patent and that said Letters Patent is hereby corrected as shown below:

Column 4, line 38,   cancel "characterized in that" and substitute --wherein--.

Column 4, line 45,   cancel "characterized in that" and substitute --wherein--.

Signed and Sealed this

Twenty-fifth Day of May, 1999

Attest:

Q. TODD DICKINSON

*Attesting Officer*   *Acting Commissioner of Patents and Trademarks*